(12) United States Patent
Kajiyama et al.

(10) Patent No.: US 9,746,435 B2
(45) Date of Patent: Aug. 29, 2017

(54) NONDESTRUCTIVE INSPECTION APPARATUS AND INSPECTION SYSTEM OF STRUCTURE

(71) Applicant: V TECHNOLOGY CO., LTD., Yokohama-shi (JP)

(72) Inventors: Koichi Kajiyama, Yokohama (JP); Michinobu Mizumura, Yokohama (JP); Yoshinori Ogawa, Yokohama (JP)

(73) Assignee: V TECHNOLOGY CO., LTD., Yokohama-Shi (JP)

( * ) Notice: Subject to any disclaimer, the term of this patent is extended or adjusted under 35 U.S.C. 154(b) by 459 days.

(21) Appl. No.: 14/475,327

(22) Filed: Sep. 2, 2014

(65) Prior Publication Data

US 2015/0063410 A1  Mar. 5, 2015

(30) Foreign Application Priority Data

Sep. 3, 2013  (JP) ................................. 2013-182357

(51) Int. Cl.
   *G01N 17/00* (2006.01)
   *G01N 3/60* (2006.01)
   *G01N 25/72* (2006.01)
   *G02B 26/10* (2006.01)

(52) U.S. Cl.
   CPC ............. *G01N 25/72* (2013.01); *G02B 26/10* (2013.01)

(58) Field of Classification Search
   None
   See application file for complete search history.

(56) References Cited

U.S. PATENT DOCUMENTS

2006/0191622 A1* 8/2006 Ritter .................... G01N 25/72
                                                         156/64

FOREIGN PATENT DOCUMENTS

JP    2001-201474 A    7/2001
JP     2001201474 A  *  7/2001

* cited by examiner

*Primary Examiner* — Erica Lin
(74) *Attorney, Agent, or Firm* — McDermott Will & Emery LLP

(57) ABSTRACT

A nondestructive inspection apparatus of a structure includes: an inspection apparatus body 1 provided with an infrared light irradiation unit irradiating a structure 3 to be inspected with heating infrared light, a temperature variation measuring unit measuring a variation in temperature of the structure due to the irradiation with infrared light from the infrared light irradiation unit, a drive-control-and-accumulation unit performing drive control of the infrared light irradiation unit and the temperature variation measuring unit and performing data accumulation; and a self-running mechanism unit 2 enabling the inspection apparatus body 1 to move along the structure 3. The structure 3 is inspected for an internal defect by irradiating the structure 3 with heating infrared light while the apparatus moves along the structure 3 through the use of the self-running mechanism unit 2 and measuring the variation in temperature of the structure 3 due to the irradiation with infrared light.

20 Claims, 10 Drawing Sheets

NONDESTRUCTIVE INSPECTION APPARATUS AND INSPECTION SYSTEM OF STRUCTURE

BACKGROUND OF THE INVENTION

1. Field of the Invention

The present invention relates to a nondestructive inspection apparatus that inspects a structure for internal defects by irradiating the structure to be inspected with infrared light, and more particularly, relates to a nondestructive inspection apparatus and an inspection system of a structure that automatically inspect the structure for internal defects over a wide range of the structure by irradiating the structure with heating infrared light while the nondestructive inspection apparatus moves along the structure to be inspected through the use of a self-running mechanism unit and measuring a variation in temperature of the structure due to the irradiation with infrared light.

2. Description of Related Art

Such a conventional apparatus for inspecting of a structure for an internal defect includes: an infrared light source that irradiates a structure with infrared light; an infrared light irradiation time controller that is connected to the infrared light source; an imaging unit that is connected to the infrared light irradiation time controller and that takes an image of the structure irradiated by the infrared light source; an image accumulating device that is connected to the imaging unit and that accumulates the images taken with the imaging unit; and an image analyzing device that is connected to the infrared light irradiation time controller and the image accumulating device, and that analyzes the images accumulated in the image accumulating device (for example, see Japanese Patent Application Laid-Open Publication No. 2001-201474).

However, in the internal defect inspection apparatus of the structure, disclosed in Japanese Patent Application Laid-Open Publication No. 2001-201474, for example, when the degradation of an internal wall surface of a tunnel, as a structure to be inspected, is inspected, at least the infrared light source and the imaging unit are mounted on a movable vehicle (carrier vehicle) and the inspection is carried out by irradiating the internal wall surface of the tunnel with infrared light from the infrared light source while driving the carrier vehicle to move at a constant speed in the tunnel. In this case, since the carrier vehicle runs in the tunnel, it may hinder the movement of other vehicles. In order to avoid this hindrance, a time zone in which the number of passing vehicles is small, such as night time, has to be selected or the frequency of performing the degradation inspection has to be lowered. In addition, since a driver of the carrier vehicle is necessary and an operator who makes the wide range of the internal wall surface of the tunnel irradiated with infrared light is also necessary in order to inspect the entire range of the internal wall surface of the tunnel, automatic inspection is not possible.

Therefore, the invention is made to solve this problem and an object of the invention is to provide a nondestructive inspection apparatus and an inspection system of a structure that automatically inspect the structure for internal defects over a wide range of the structure by irradiating the structure with heating infrared light while the nondestructive inspection apparatus moves along the structure to be inspected through the use of a self-running mechanism unit and measuring a variation in temperature of the structure due to the irradiation with infrared light.

SUMMARY OF THE INVENTION

In order to achieve the above-mentioned object, according to the present invention, there is provided a nondestructive inspection apparatus of a structure, including: an infrared light irradiation unit that irradiates a structure to be inspected with heating infrared light; a temperature variation measuring unit that measures a variation in temperature of the structure due to the irradiation with infrared light from the infrared light irradiation unit; a drive-control-and-accumulation unit that performs drive control of the infrared light irradiation unit and the temperature variation measuring unit and performs data accumulation; and a self-running mechanism unit that enables a casing, on which the infrared light irradiation unit, the temperature variation measuring unit, and the drive-control-and-accumulation unit are mounted, to move along the structure, in which the structure is inspected for an internal defect by irradiating the structure with heating infrared light while the nondestructive inspection apparatus moves along the structure to be inspected through the use of the self-running mechanism unit and measuring the variation in temperature of the structure due to the irradiation with infrared light.

The infrared light irradiation unit and the temperature variation measuring unit may be independently rotatable about a horizontal rotation shaft.

The infrared light irradiation unit may be an infrared laser that oscillates a heating laser beam.

The temperature variation measuring unit may be a laser beam receiving-and-emitting unit that irradiates the structure with a measuring laser beam and that detects the reflected beam thereof to determine the reflectance of the structure.

The temperature variation measuring unit may be an infrared light detector that determines an amount of infrared light emitted from the structure to measure the variation in temperature of the structure.

The self-running mechanism unit may be configured to support a support member of the casing using a guide rail installed on a road surface extending along the structure and to enable the support member to move on the road surface by guidance of the guide rail.

The self-running mechanism unit may include a movable support member that is formed in an arch shape along an internal wall surface of the structure in which the internal wall surface has a cross-sectional shape of a semi-circular arc and that supports the casing, and may be configured to enable pedestal members at both ends of the movable support member to move on the road surface by themselves.

The casing may include a monitoring camera that monitors the front side in the moving direction thereof.

The self-running mechanism unit may be configured to move forward and backward along the structure and at least the infrared light irradiation unit and the temperature variation measuring unit may be disposed as a pair for each direction of the movements.

In the nondestructive inspection apparatus of a structure according to the present invention, the infrared light irradiation unit irradiates the structure to be inspected with heating infrared light, the temperature variation measuring unit measures the variation in temperature of the structure due to the irradiation with infrared light from the infrared light irradiation unit, the drive-control-and-accumulation unit performs drive control of the infrared light irradiation unit and the temperature variation measuring unit and performs data accumulation, the self-running mechanism unit enables the casing, on which the infrared light irradiation unit, the temperature variation measuring unit, and the drive-control-and-accumulation unit are mounted, to move along the structure, and the structure can be automatically inspected for an internal defect over a wide range of the structure by irradiating the structure with heating infrared light while the nondestructive inspection apparatus moves along the structure to be inspected through the use of the self-running mechanism unit and measuring the variation in temperature of the structure due to the irradiation with infrared light. Accordingly, it is possible to nondestructively inspect the structure at any time of a day without hindering the movement of other vehicles. Since the labor of an operator or the like is not necessary, it is possible to reduce inspection costs.

According to the present invention, there is provided an inspection system of a structure including: a nondestructive inspection apparatus including an infrared light irradiation unit that irradiates a structure to be inspected with heating infrared light, a temperature variation measuring unit that measures a variation in temperature of the structure due to the irradiation with infrared light from the infrared light irradiation unit, a drive-control-and-accumulation unit that performs drive control of the infrared light irradiation unit and the temperature variation measuring unit and performs data accumulation, a self-running mechanism unit that enables a casing, on which the infrared light irradiation unit, the temperature variation measuring unit, and the drive-control-and-accumulation unit are mounted, to move along the structure, and a communication unit that transmits inspection data acquired by the drive-control-and-accumulation unit to the outside, in which the structure is inspected for an internal defect by irradiating the structure with heating infrared light while the nondestructive inspection apparatus moves along the structure to be inspected through the use of the self-running mechanism unit and measuring the variation in temperature of the structure due to the irradiation with infrared light; a relay that receives the inspection data transmitted from the nondestructive inspection apparatus; a control center that receives the inspection data transmitted from the nondestructive inspection apparatus and processes the inspection data; and a bidirectional communication network that is disposed between the relay and the control center, and transmits and receives the inspection data.

The inspection data transmitted from the nondestructive inspection apparatus may be processed and transmitted to the control center through the use of the relay.

The nondestructive inspection apparatus may be installed for each of plural structures to be inspected, and the single control center may be installed for the plural nondestructive inspection apparatuses via the bidirectional communication network.

In the inspection system of a structure according to the present invention, the nondestructive inspection apparatus of a structure can automatically inspect the structure for an internal defect over a wide range of the structure by irradiating the structure to be inspected with heating infrared light while moving along the structure through the use of the self-running mechanism unit and measuring the variation in temperature of the structure due to the irradiation with infrared light, the relay can receive the inspection data transmitted from the nondestructive inspection apparatus and can transmit and receive the inspection data via the bidirectional communication network disposed between the relay and the control center, and the control center can receive and process the inspection data transmitted from the nondestructive inspection apparatus. Accordingly, it is possible to nondestructively inspect the structure at any time of a day without hindering the movement of other vehicles. Since the labor of an operator or the like is not necessary, it is possible to reduce inspection costs.

DESCRIPTION OF PREFERRED EMBODIMENTS

Hereinafter, embodiments of the present invention will be described with reference to the accompanying drawings.

Figure 1:
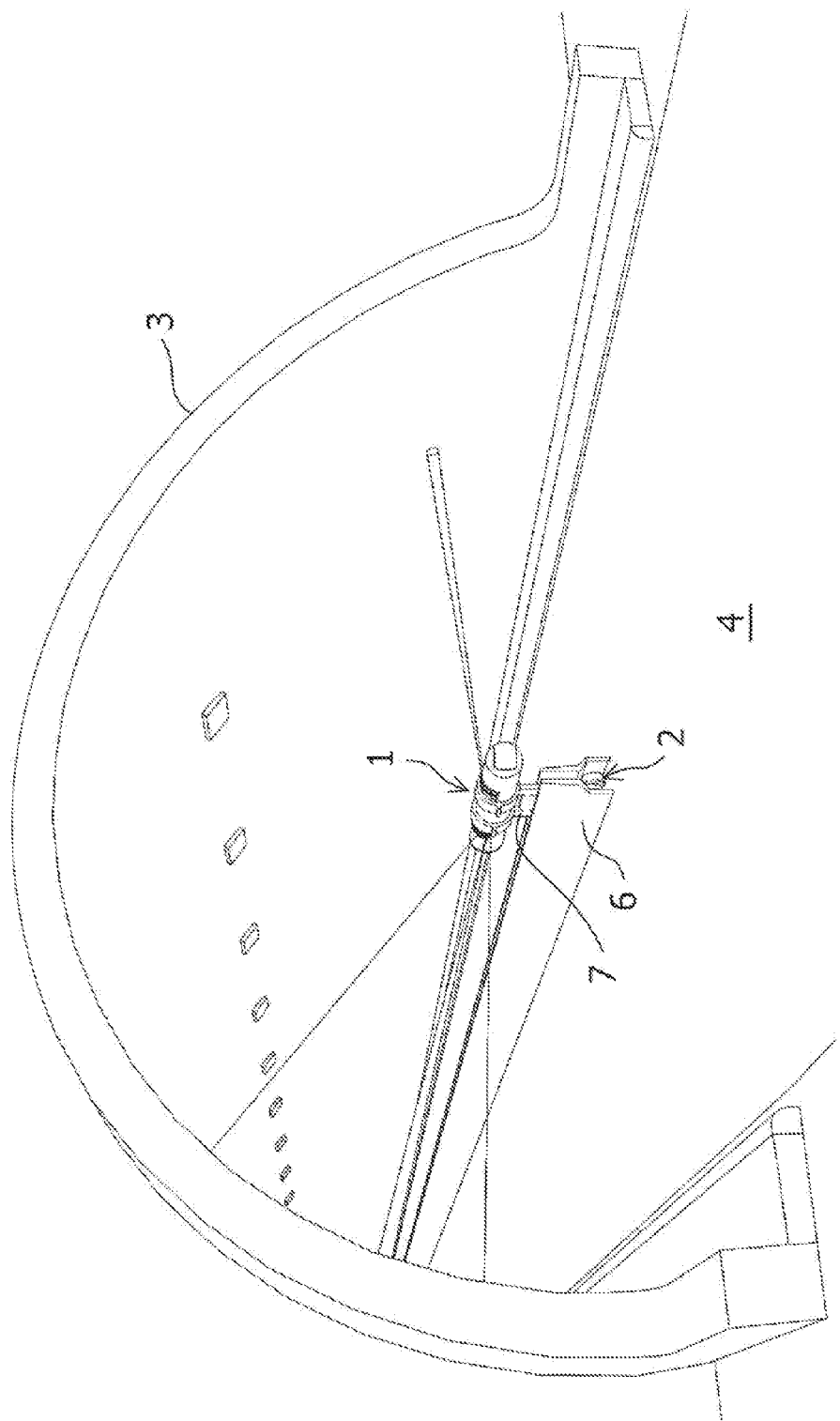
FIG. 1 is a perspective view schematically illustrating an arranged state of a nondestructive inspection apparatus of a structure according to the present invention.

FIG. 1 is a perspective view schematically illustrating an arranged state of a nondestructive inspection apparatus of a structure according to the present invention. The nondestructive inspection apparatus serves to inspect the structure for internal defects by irradiating the structure to be inspected (a structure such as a tunnel or an elevated bridge) with infrared light and includes an inspection apparatus body 1 and a self-running mechanism unit 2. Reference numeral 3 denotes a tunnel as a structure to be inspected in which the nondestructive inspection apparatus according to the invention is disposed and reference numeral 4 denotes a road extending from the outside to the inside of the tunnel 3.

Figure 2:
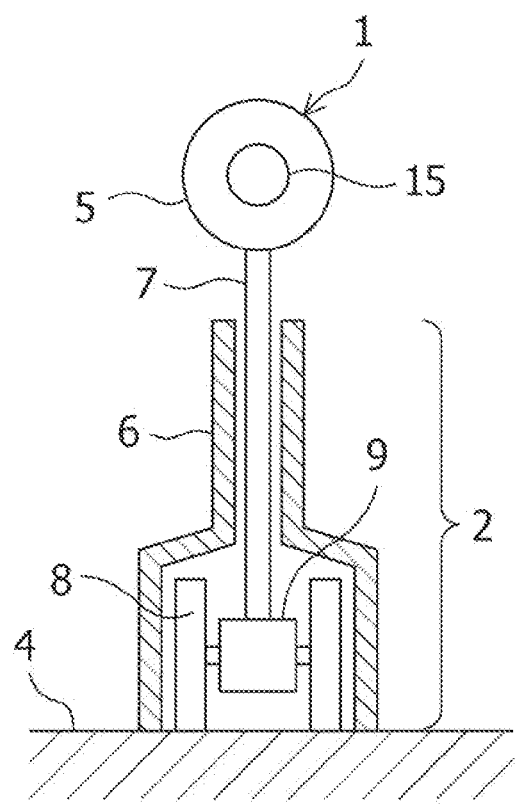
FIG. 2 is a cross-sectional view illustrating a principal part of a self-running mechanism unit of the nondestructive inspection apparatus, a guide rail on a road surface being crossed.

The self-running mechanism unit 2 enables a casing 5 (see FIG. 2) of the inspection apparatus body 1 to move along the tunnel 3 and supports, as illustrated in FIG. 2, a support member 7 of the casing 5 using a guide rail 6, which is installed at the center of the road 4 extending along the tunnel 3 illustrated in FIG. 1 and serves as a median strip. The lower end of the support member 7 having the casing 5 mounted on the upper end extends toward the road surface of the road 4 and driving wheels 8 are disposed at the lower end thereof. A swelling part is formed at the lower end of the guide rail 6, and the driving wheels 8 are disposed in the swelling part and rotated by an electric motor 9. With the rotation of the driving wheels 8, the support member 7 can run by itself in one direction or both forward and backward directions on the road surface by the guidance of the guide rail 6. That is, the self-running mechanism unit 2 includes the support member 7, the electric motor 9, and the driving wheels 8 and is configured to movable forward and backward along the tunnel 3. The supply of power to the electric motor 9 can be realized by wiring a power transmission line using the internal space of the guide rail 6 and bringing a power receiver into sliding contact with the power transmission line, similarly to subways.

Figure 3:
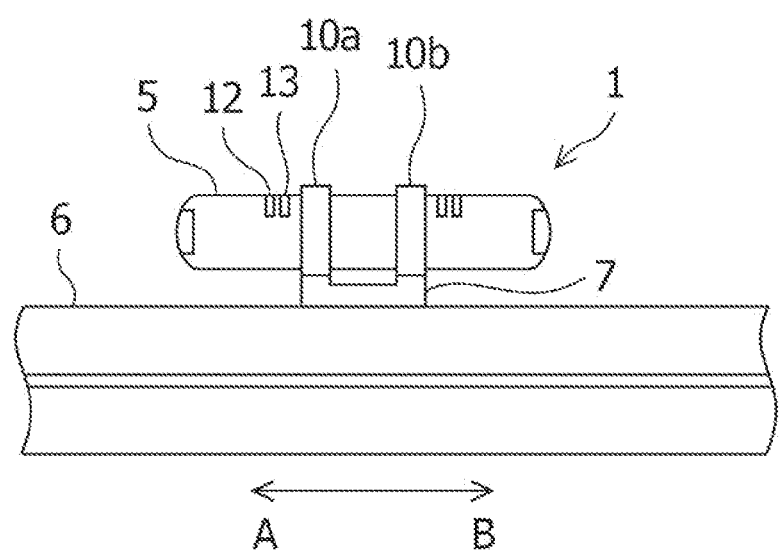
FIG. 3 is a side view illustrating an inspection apparatus body of the nondestructive inspection apparatus.

The inspection apparatus body 1 is supported by the self-running mechanism unit 2 so as to be movable along the tunnel 3. The inspection apparatus body 1 serves to irradiate the internal wall surface of the tunnel 3 as a structure with heating infrared light, to measure a variation in temperature of the internal wall surface of the tunnel 3 due to the irradiation with infrared light, and to accumulate data. As illustrated in FIG. 3, the casing 5 is mounted on the upper end of the support member 7 held by the guide rail 6. The casing 5 has, for example, a cylindrical shape and receives therein an infrared light irradiation unit 12, a temperature variation measuring unit 13, a drive-control-and-accumulation unit 14, and the like to be described later. The casing 5 is secured by fixing bands 10a and 10b at two positions of the upper end of the support member 7. In FIG. 3, the inspection apparatus body 1 can move forward and backward in the directions of arrows A and B through the use of the self-running mechanism unit 2 illustrated in FIG. 2.

Figure 4:
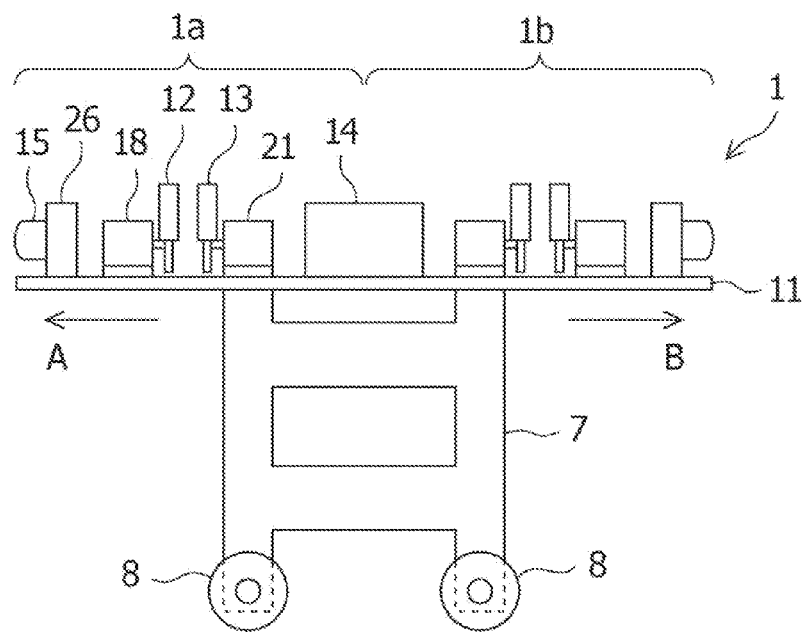
FIG. 4 is an enlarged side view illustrating an internal configuration of the inspection apparatus body from which a casing is detached.

FIG. 4 is an enlarged side view illustrating an internal configuration of the inspection apparatus body 1 from which the casing 5 is detached. In this example, a first inspection section 1a in one half in the longitudinal direction on the top surface of a base member 11 and a second inspection section 1b in the other half are disposed in a line. The first inspection section 1a and the second inspection section 1b are disposed as a pair so that each section inspects the structure for an internal defect in each moving direction when the inspection apparatus body 1 moves forward and backward. In FIG. 4, the first inspection section 1a performs inspection when the inspection apparatus body 1 moves to the left side of the drawing (in the direction of arrow A) and the second inspection section 1b performs inspection when the inspection apparatus body 1 moves to the right side of the drawing (in the direction of arrow B). Here, the first inspection section 1a will be representatively described below. The second inspection section 1b has the same configuration as the first inspection section 1a. When the inspection is performed only when the inspection apparatus body 1 moves in one of the direction of arrow A and the direction of arrow B, only one of the first inspection section 1a and the second inspection section 1b may be disposed. In this case, the inspection apparatus body 1 is returned to the original position without carrying out any operation after the inspection apparatus body 1 moves in the direction of arrow A or the direction of arrow B for the inspection.

In FIG. 4, the first inspection section 1a includes the infrared light irradiation unit 12, the temperature variation measuring unit 13, the drive-control-and-accumulation unit 14, and a monitoring camera 15. Here, the drive-control-and-accumulation unit 14 is common to the first inspection section 1a and the second inspection section 1b and is disposed at the midpoint therebetween. Since infrared light is emitted from the infrared light irradiation unit 12, it is preferable that the base member 11 be formed of a material blocking infrared light so as to intercept irradiation with infrared light to the lower side thereof.

Figure 5:
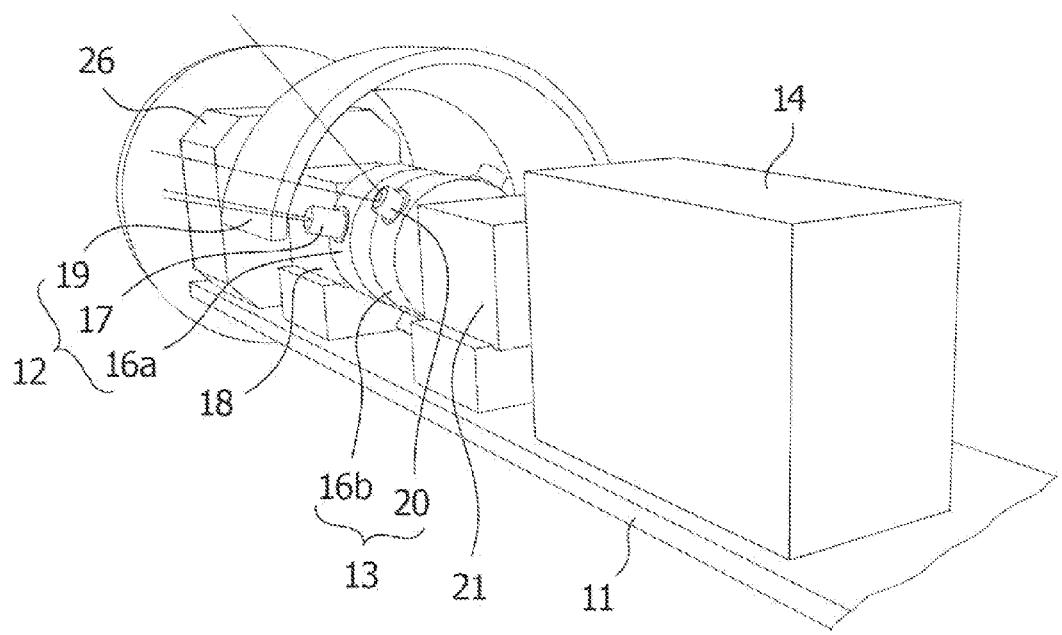
FIG. 5 is an enlarged perspective view of the principal part illustrating a part of the inspection apparatus body illustrated in FIG. 4.

The infrared light irradiation unit 12 serves to irradiate a structure to be inspected with heating infrared light and includes, for example, an infrared laser that oscillates a heating laser beam. The infrared laser oscillates a heating laser beam with a wavelength of about 1.5 μm and a beam diameter of about 0.010 m. The surface of the structure is heated by the irradiation with the heating laser beam. As shown in FIG. 5, the infrared light irradiation unit 12 has one or more infrared laser chips 17 on the outer circumferential surface of a first drum 16a having a horizontal rotation shaft, and the first drum 16a is rotated by an electric motor 18 connected to the rotation shaft thereof. Outside the first drum 16a, a condensing lens 19 formed to have a semi-circular cross-section and formed in a semi-circular arc shape so as to cover the first drum 16a is arranged with a support fitting (not illustrated). The emitted heating laser beam is condensed in the form of a beam by the condensing lens 19, and the surface of the structure is scanned with the beam. The infrared laser chip 17 includes a light emitting-and-receiving element and a laser chip.

The temperature variation measuring unit 13 serves to measure a variation in temperature of the structure due to the irradiation with infrared light from the infrared light irradiation unit 12 and includes, for example, a laser beam receiving-and-emitting unit that determines the reflectance of the structure by irradiating the structure with a measuring laser beam and detecting the reflected beam. The laser beam receiving-and-emitting unit oscillates a measuring laser beam with a wavelength of about 0.5 μm and a beam diameter of about 0.001 m and detects the reflected beam from the structure. The reflectance of the structure is determined by the detection of the reflected beam and the thermal conductivity can be determined using the temperature dependency of the optical reflectance of a material. This inspection principle is called "optical heating thermoreflectance method". As illustrated in FIG. 5, the temperature variation measuring unit 13 includes plural laser beam receiving-and-emitting chips 20 on the outer circumferential surface of a second drum 16b having a horizontal rotation shaft and the second drum 16b is rotated by an electric motor 21 connected to the rotation shaft thereof. Outside the second drum 16b, a condensing lens (not illustrated, the same as the condensing lens 19 of the infrared light irradiation unit 12) formed to have a semi-circular cross-section and formed in a semi-circular arc shape so as to cover the second drum 16b is arranged. In this case, the emitted measuring laser beam is condensed in the form of a beam, and the surface of the structure is scanned with the beam. The laser beam receiving-and-emitting chip 20 includes a light emitting-and-receiving element and a laser chip.

Regarding the arrangement of the infrared light irradiation unit 12 and the temperature variation measuring unit 13, since the structure is irradiated with heating infrared light by the infrared light irradiation unit 12 and then the variation in temperature of the structure due to the irradiation with infrared light is measured by the temperature variation measuring unit 13, the infrared light irradiation unit 12 is located on the front side in the moving direction.

The infrared light irradiation unit 12 and the temperature variation measuring unit 13 are independently rotatable about the horizontal rotation shaft. That is, the electric motor 18 connected to the rotation shaft of the first drum 16a of the infrared light irradiation unit 12 and the electric motor 21 connected to the rotation shaft of the second drum 16b of the temperature variation measuring unit 13 are independently controlled in rotation.

Figure 6:
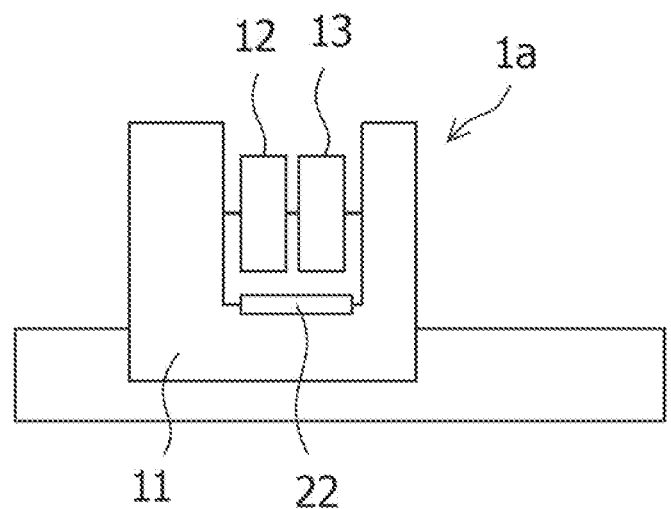
FIG. 6 is an explanatory diagram schematically illustrating an example in which a rotation of an infrared light irradiation unit and a temperature variation measuring unit of the inspection apparatus body is detected.

In this case, the rotations of the infrared light irradiation unit 12 and the temperature variation measuring unit 13 are detected as illustrated in FIG. 6. For example, a high-reflectance member 22 is disposed on the top surface of the base member 11 having the infrared light irradiation unit 12 and the temperature variation measuring unit 13 mounted thereon, reflected beams of laser beams emitted from the infrared laser chip 17 and the laser beam receiving-and-emitting chip 20 are received, and it is detected whether the infrared laser chip 17 and the laser beam receiving-and-emitting chip 20 are rotated and the rotation angles are measured. Not limited to this, an encoder may be provided in the rotation shaft of the first drum 16a or the second drum 16b and the rotations may be detected using a known method.

Figure 7:
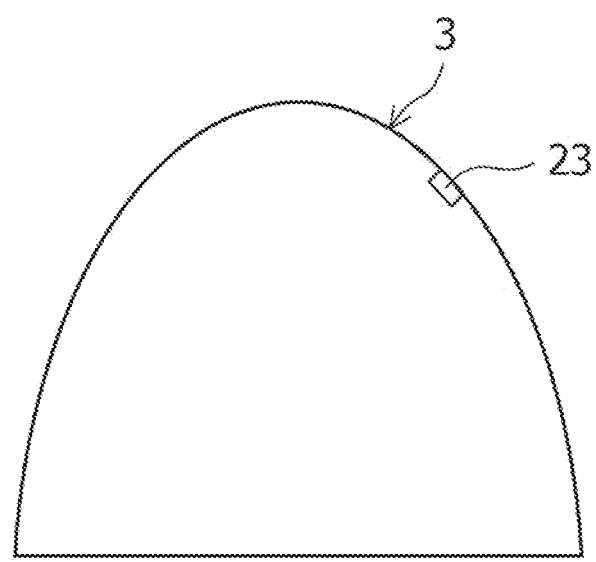
FIG. 7 is an explanatory diagram schematically illustrating an example in which a rotation angle of the infrared light irradiation unit and the temperature variation measuring unit of the inspection apparatus body with respect to a tunnel is detected.

The rotation angles of the infrared light irradiation unit 12 and the temperature variation measuring unit 13 with respect to the internal wall surface of the tunnel 3 are measured as illustrated in FIG. 7. For example, a high-reflectance member 23 is disposed at a specific position or at positions with constant spacing on the internal wall surface of the tunnel 3, the reflected beams of the laser beams emitted from the infrared laser chip 17 and the laser beam receiving-and-emitting chip 20 are received, and the rotation angles of the infrared laser chip 17 and the laser beam receiving-and-emitting chip 20 are measured. At this time, the specific position at which the high-reflectance member 23 is disposed can be set to the zero point position of the rotation angles of the infrared laser chip 17 and the laser beam receiving-and-emitting chip 20. It is assumed that the high-reflectance member 23 does not rise in temperature due to the absorption of the heating infrared light from the infrared light irradiation unit 12.

The drive-control-and-accumulation unit 14 serves to perform drive control of the infrared light irradiation unit 12 and the temperature variation measuring unit 13 and to perform data accumulation, and includes a power supply circuit that drives the infrared laser chip 17 and the laser beam receiving-and-emitting chip 20, a power supply circuit that drives the electric motors 18 and 21, and a data accumulating-and-transmitting circuit that accumulates inspection data acquired by the operations of the infrared light irradiation unit 12 and the temperature variation measuring unit 13.

The monitoring camera 15 serves to monitor the front side in the moving direction of the inspection apparatus body 1 and is attached at the front end or the rear end of the casing 5 formed in a cylindrical shape toward the front side in the moving direction so as to face the lens. The situation, obstacles, and the like on the front side in the moving direction of the inspection apparatus body 1 can be monitored by the monitoring camera 15. The tunnel wall can be inspected by the use of a fish-eye lens.

Figure 8:
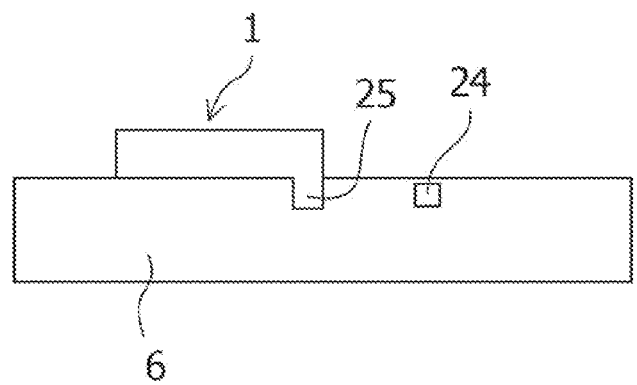
FIG. 8 is an explanatory diagram schematically illustrating an example in which a moved position of the nondestructive inspection apparatus relative to the guide rail on the road surface is detected.

The moved position of the inspection apparatus body 1 having the above-mentioned configuration with respect to the guide rail 6 is detected as illustrated in FIG. 8. For example, the high-reflectance member 24 is disposed at a specific position or at positions with constant spacing of the guide rail 6, the light receiving-and-emitting unit 25 emitting light to the high-reflectance member 24 and receiving the reflected light thereof is disposed in a part of the support member 7 of the inspection apparatus body 1, the reflected light from the high-reflectance member 24 is detected, and it is detected at what position in the longitudinal direction of the guide rail 6 the inspection apparatus body 1 is located. Accordingly, it is possible to detect the position of the inspection apparatus body 1 moving along the structure to be inspected. Instead of the high-reflectance member 24, a through-hole may be formed at the position corresponding thereto and the light receiving-and-emitting unit 25 may detect the position using light passing through the through-hole.

Figure 9:
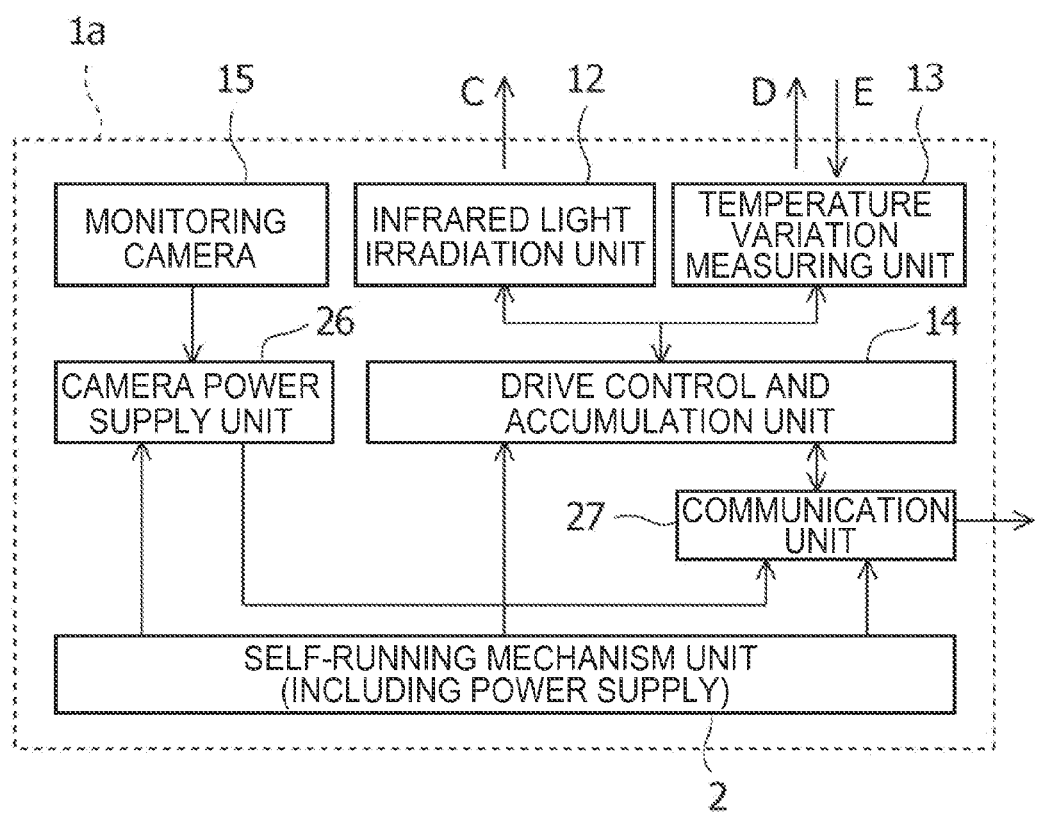
FIG. 9 is a block diagram illustrating a configuration and a function of the nondestructive inspection apparatus.

FIG. 9 is a block diagram illustrating the configuration and the function of the nondestructive inspection apparatus having the above-mentioned configuration. The nondestructive inspection apparatus includes an infrared light irradiation unit 12, a temperature variation measuring unit 13, a drive-control-and-accumulation unit 14, a self-running mechanism unit 2, a monitoring camera 15, a camera power supply unit 26, and a communication unit 27. FIG. 9 illustrates only the part of the first inspection section 1a illustrated in FIG. 4 in the inspection apparatus body 1 illustrated in FIG. 3 and does not illustrate the part of the second inspection section 1b. The second inspection section 1b commonly includes the self-running mechanism unit 2 and the drive-control-and-accumulation unit 14 and the other parts are the same as the configuration and the function of the first inspection section 1a illustrated in FIG. 9.

The infrared light irradiation unit 12 serves to irradiate the structure to be inspected with a heating laser beam, includes, for example, a high-power infrared laser that oscillates a heating laser beam, and oscillates the heating laser beam with a wavelength of about 1.5 µm as indicated by arrow C. The temperature variation measuring unit 13 serves to measure a variation in temperature of the structure due to the irradiation with the infrared light from the infrared light irradiation unit 12, includes, for example, a low-power laser beam receiving-and-emitting unit that determines the reflectance of the structure by irradiating the structure with a measuring laser beam and detecting the reflected beam thereof, oscillates a measuring laser beam with a wavelength of about 0.5 µm as indicated by arrow D, and detects the reflected beam reflected from the structure as indicated by arrow E.

The drive-control-and-accumulation unit 14 serves to perform the drive control of the infrared light irradiation unit 12 and the temperature variation measuring unit 13 and the data accumulation. The drive-control-and-accumulation unit 14 includes: a power supply circuit that drives the infrared laser of the infrared light irradiation unit 12 or the laser beam receiving-and-emitting unit of the temperature variation measuring unit 13; an inspection logic circuit that accumulates the data acquired by the infrared light irradiation unit 12 and the temperature variation measuring unit 13; and the like.

The self-running mechanism unit 2 serves to enable the casing 5 (see FIG. 3), on which the infrared light irradiation unit 12, the temperature variation measuring unit 13, and the drive-control-and-accumulation unit 14 are mounted, to move along the structure, and includes the electric motor 9 illustrated in FIG. 2 and a circuit that sends power supplied from the outside to the electric motor 9 so as to control the rotation of the driving wheels 8. The self-running mechanism unit 2 also includes a power supply circuit that supplies power to the drive-control-and-accumulation unit 14, the camera power supply unit 26 to be described later, and the communication unit 27.

The monitoring camera 15 serves to monitor the front side in the moving direction of the inspection apparatus body 1, takes an image with power supplied from the camera power supply unit 26, and collects the image data.

The communication unit 27 serves to send the inspection data acquired by the drive-control-and-accumulation unit 14 and the image data collected by the monitoring camera 15 and transmitted via the camera power supply unit 26 to the outside (for example, a relay 51 illustrated in FIG. 16), and the communication unit 27 is operated with power supplied from the power supply circuit of the self-running mechanism unit 2.

While the nondestructive inspection apparatus moves along the structure to be inspected through the use of the self-running mechanism unit 2, the structure is irradiated with heating infrared light by the infrared light irradiation unit 12, the variation in temperature of the structure due to the irradiation with the infrared light from the infrared light irradiation unit 12 is measured by the temperature variation measuring unit 13, and the drive control of the infrared light irradiation unit 12 and the temperature variation measuring unit 13 and the data accumulation are performed by the drive-control-and-accumulation unit 14, so that the structure is inspected for an internal defect.

Figures 10A, 10B, 10C:
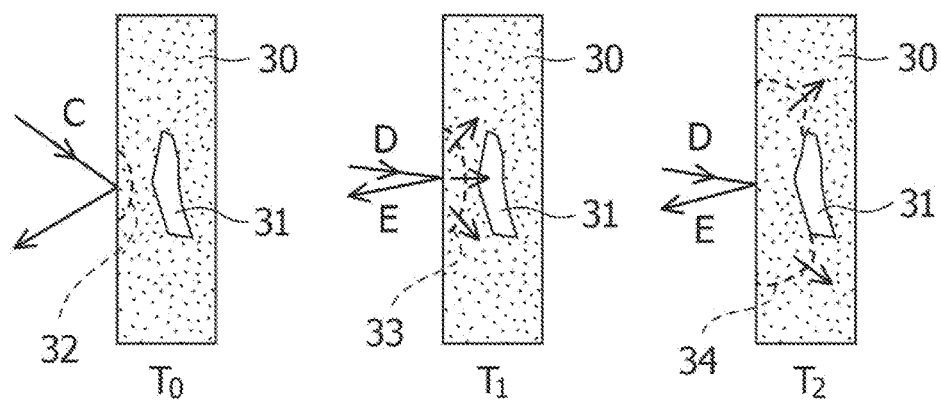
FIGS. 10A to 10C are explanatory diagrams illustrating an inspection principle of the nondestructive inspection apparatus.
Figure 11:
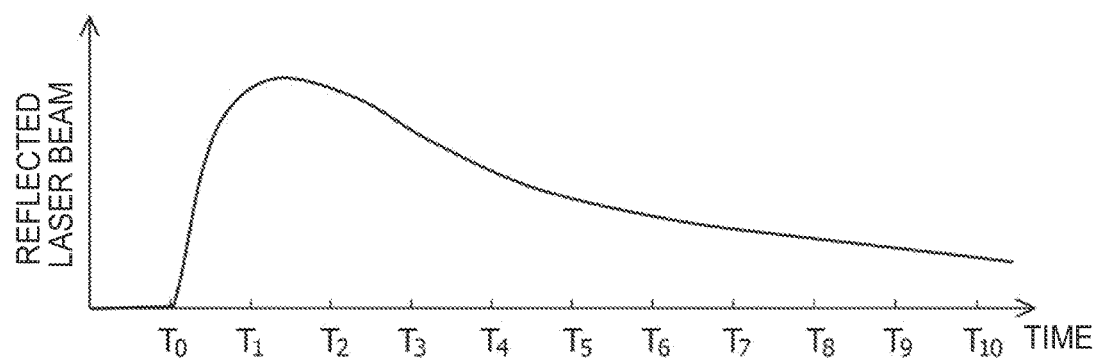
FIG. 11 is a graph illustrating the inspection principle of the nondestructive inspection apparatus.

Next, the inspection principle of the nondestructive inspection apparatus according to the present invention will be described below. FIGS. 10A to 10C are explanatory diagrams illustrating the inspection principle of the nondestructive inspection apparatus and FIG. 11 is a graph illustrating the inspection principle of the nondestructive inspection apparatus. The inspection principle is to irradiate a structure with light, to measure the reflected light thereof, and to determine thermal conductivity using temperature dependency of the optical reflectance of a material, and is called "optical heating thermoreflectance method". It is possible to find out a crack or a void in the structure using this inspection principle by determining the optical reflectance of a reflected light measuring position of the structure to be inspected, calculating local thermal conductivity from the transient characteristic, and mapping the resultant.

In FIG. 10A, it is assumed that a crack 31 or a void is present in a structure 30 to be inspected. First, the surface of the structure 30 is irradiated with a heating laser beam from the infrared light irradiation unit 12 as indicated by arrow C (time $T_0$). At this time, the beam diameter of the heating laser beam (C) is set to about 0.010 m, which is about ten times the beam diameter of a measuring laser beam to be described later. A part 32 on the surface of the structure 30, to which the heating laser beam (C) is brought, rises in temperature and the heat diffuses into the surrounding. Thereafter, in FIG. 10B, the surface of the structure 30 is irradiated with the measuring laser beam by the temperature variation measuring unit 13 as indicated by arrow D, and the reflected beam reflected as indicated by arrow E is measured (time $T_1$). At this time, the beam diameter of the measuring laser beam (D) is set to about 0.001 m, which is about ⅒ times the beam diameter of the heating laser beam (C). Heat in the part 32, to which the heating laser beam (C) has been brought, diffuses with the lapse of time in the meantime and the heat diffuses into the surrounding like a diffused area 33. Thereafter, in FIG. 10C, a next measuring laser beam is emitted from the temperature variation measuring unit 13 as indicated by arrow D and the reflected beam reflected as indicated by arrow E is measured (time $T_2$). At this time, the heat in the part 32, to which the heating laser beam (C) has been brought at time $T_0$, further diffuses with the lapse of time in the meantime and the heat diffuses into the surrounding like a diffused area 34.

Thereafter, at time $T_1$ to $T_{10}$ with predetermined time intervals, the heated part 32 of the surface of the structure 30 is irradiated with a measuring laser beam as indicated by arrow D and the reflected beam reflected as indicated by arrow E is measured, as described above. The measurement results are arranged in the graph illustrated in FIG. 11. FIG. 11 is a graph in which the horizontal axis represents the time and the vertical axis represents the intensity of a reflected laser beam, and illustrates a variation state of the reflected beam in the part in which heat diffuses, like diffused areas 33 and 34 illustrated in FIGS. 10B and 10C, by irradiating the surface of the structure 30 with a heating laser beam at time $T_0$ to heat the part 32, irradiating the heated part 32 of the structure 30 with the measuring laser beam at times $T_1$ to $T_{10}$, and measuring the reflected beam thereof. In this case, within the beam width of the heating laser beam (C) applied at time $T_0$, the measuring laser beam (D) is applied ten times from times $T_1$ to $T_{10}$ and the reflected beam thereof is measured for each time.

By measuring the reflected beam as illustrated in FIG. 11, it is possible to determine the reflectance of the heated part 32 on the surface of the structure 30. Here, according to the "optical heating thermoreflectance method", it is possible to determine the thermal conductivity using the temperature dependency of the optical reflectance of a material. Accordingly, when the graphs obtained by measuring the reflected beam, as illustrated in FIG. 11, with different positions are arranged in accordance with the measurement parts, it can be seen that the thermal conductivity of a position varies when the measurement result is different from that of the surrounding parts at the position, so that it can be seen that a crack 31 or a void is present at the position.

The heating of the structure to be inspected and the measuring of the reflected beam are periodically performed every day or every predetermined period, and it can be seen that a particular state occurs on the surface of the structure or in the structure when measurement data different from the previous measurement data is acquired with the lapse of time, so that it is possible to inspect the structure for an internal defect.

Next, the usage and operation of the nondestructive inspection apparatus having the above-mentioned configuration will be described below. First, in FIG. 1, the self-running mechanism unit 2 is assembled using the guide rail 6 disposed on the road 4 in the tunnel 3, for example, as the structure to be inspected, and the inspection apparatus body 1 is set at the center on the road 4 in the tunnel 3. In this state, the self-running mechanism unit 2 is supplied with power from the outside to drive the infrared light irradiation unit 12 and the temperature variation measuring unit 13 illustrated in FIGS. 3 and 4, the first drum 16a and the second drum 16b illustrated in FIG. 5 are made to independently rotate to cause the infrared laser chip 17 and the laser beam receiving-and-emitting chip 20 to rotate, and the heating laser beam is oscillated to the internal wall surface of the tunnel 3 or the measuring laser beam is applied thereto. At the same time, the electric motor 9 of the self-running mechanism unit 2 illustrated in FIG. 2 is driven to rotate the driving wheels 8, the inspection apparatus body 1 is moved at a constant speed in the direction of arrow A or the direction of arrow B along the guide rail 6 as illustrated in FIG. 3 so as to move in one way or move forward and backward over the entire length of the tunnel 3. It is preferable that the rotation of the laser beam receiving-and-emitting chip 20 for measurement be faster than the rotation of the infrared laser chip 17 for the heating infrared light.

The rotations and the rotation angles of the infrared laser chip 17 of the infrared light irradiation unit 12 and the laser beam receiving-and-emitting chip 20 of the temperature variation measuring unit 13 are obtained by receiving the reflected beam from the high-reflectance member 22 mounted on the top surface of the base member 11 illustrated in FIG. 6. The rotation angles of the infrared light irradiation unit 12 and the temperature variation measuring unit 13 with respect to the internal wall surface of the tunnel 3 are measured by receiving the reflected beam from the high-reflectance member 23 disposed at a specific position or at positions with constant spacing on the internal wall surface of the tunnel 3 illustrated in FIG. 7. The moved position of the inspection apparatus body 1 with respect to the guide rail 6 is detected by receiving the reflected beam from the high-reflectance member 24 disposed at a specific position or at positions with constant spacing of the guide rail 6 illustrated in FIG. 8. Accordingly, the position of the inspection apparatus body 1 moving along the tunnel 3 to be inspected is detected.

By these operations, the position of the laser beam radiates from the infrared light irradiation unit 12 and the temperature variation measuring unit 13 with respect to the internal wall surface of the tunnel 3 is specified, the position of the inspection apparatus body 1 moving along the guide rail 6 is specified, and it is possible to uniformly and automatically inspect the internal wall surface of the tunnel 3 by performing the operations illustrated in FIGS. 9 to 11. In this case, it is possible to nondestructively inspect the tunnels 3 at any time of a day without hindering the movement of other vehicles. Since the labor of an operator or the like is not necessary, it is possible to reduce inspection costs.

In the above-mentioned configuration, the temperature variation measuring unit 13 employs the laser beam receiving-and-emitting unit that determines the reflectance of the structure by irradiating the structure with a measuring laser beam and detecting the reflected beam thereof, that is, for example, the laser beam receiving-and-emitting chip 20, but the invention is not limited to this configuration. An infrared light detector that measures a variation in temperature of the structure by measuring an amount of infrared light emitted from the structure, that is, for example, an infrared camera that can perform thermography measurement, may be employed.

Figure 12:
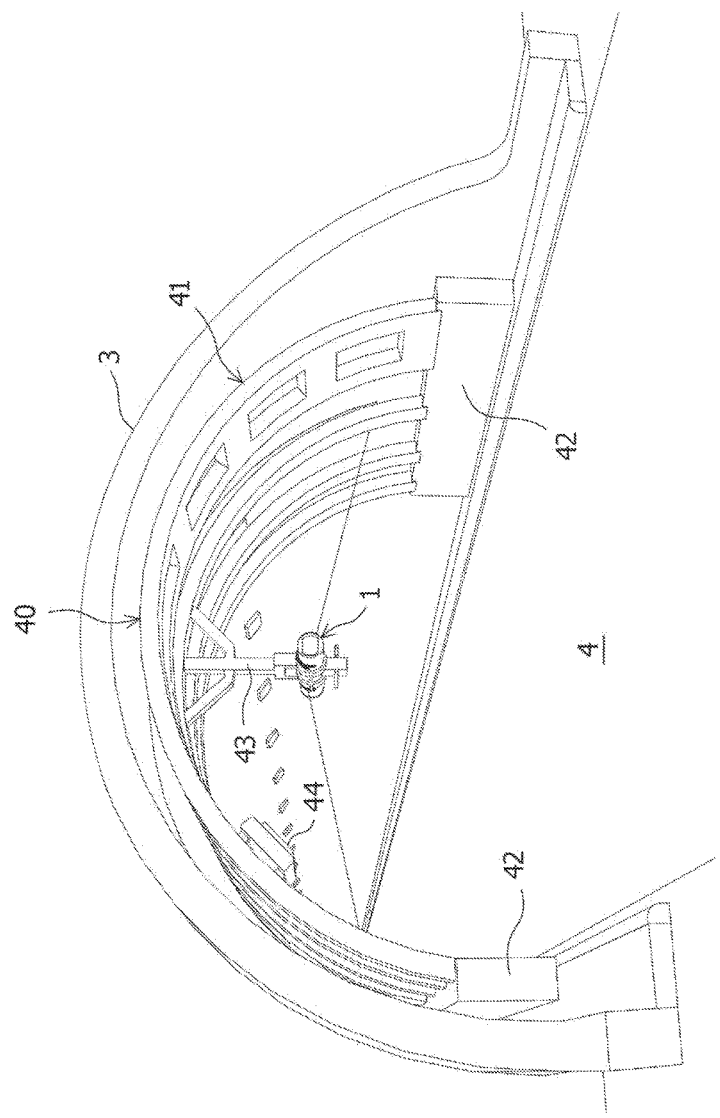
FIG. 12 is a diagram illustrating another arranged state of the nondestructive inspection apparatus and is a perspective view schematically illustrating a self-running mechanism unit according to a second embodiment of the present invention.

FIG. 12 is a diagram illustrating another arranged state of the nondestructive inspection apparatus according to the present invention and is a perspective view schematically illustrating a self-running mechanism unit according to a second embodiment of the present invention. In this embodiment, a self-running mechanism unit 40 that supports the casing 5 (see FIG. 2) of the inspection apparatus body 1 so as to be movable includes a movable support member 41 that is formed in an arch shape along the internal wall surface of the tunnel 3 as a structure having a cross-sectional shape of a semi-circular arc and that supports the casing 5. Pedestal members 42 at both ends of the movable support member 41 can run on the road surface by itself.

Figure 13:
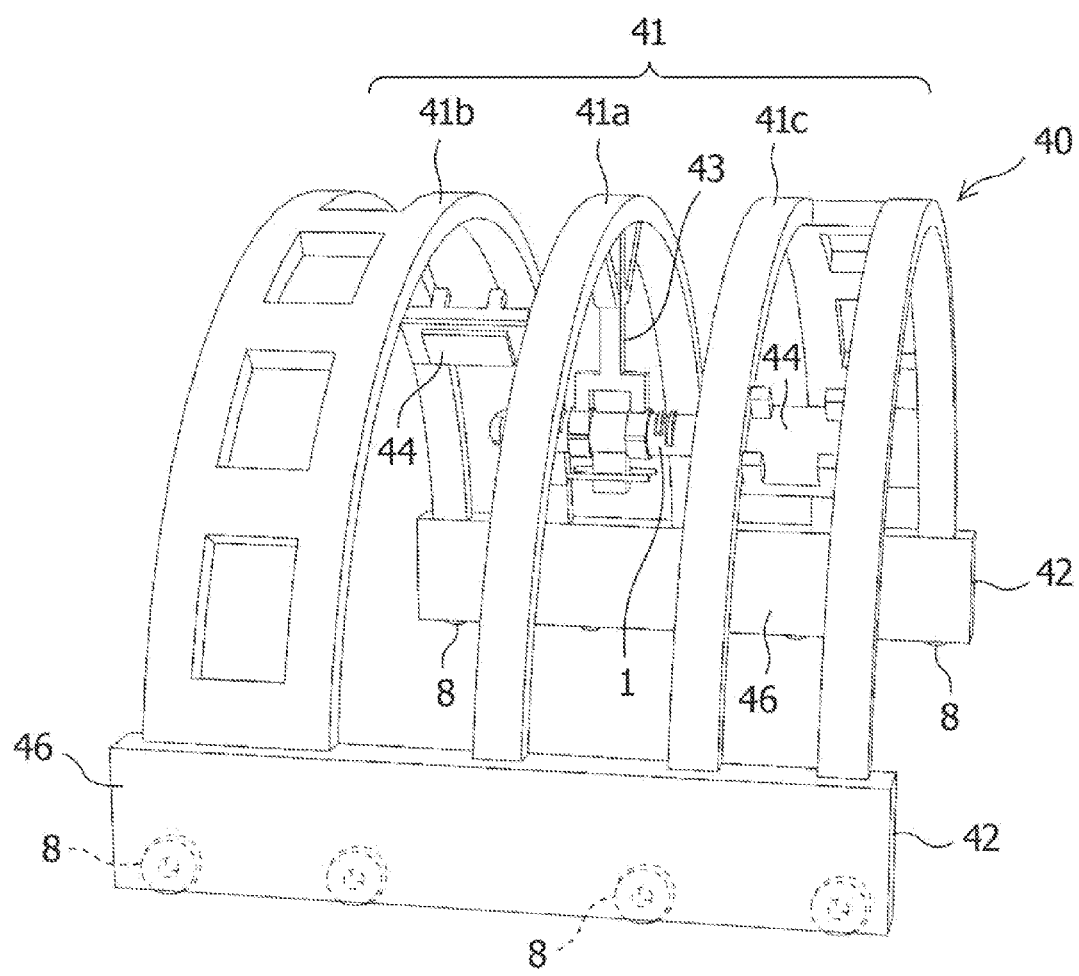
FIG. 13 is a perspective view illustrating a structure of the self-running mechanism unit according to the second embodiment.

The movable support member 41 includes a first support member 41a of an arch shape located at the center, and a second support member 41b and a third support member 41c of an arch shape located at positions spaced apart forward and backward therefrom, as illustrated in FIG. 13. A suspended support 43 is attached to the bottom surface of the center of the semi-circular arc shape of the first support member 41a as illustrated in FIG. 12, the inspection apparatus body 1 having the configuration illustrated in FIGS. 3 and 4 is supported by the lower end of the suspended support 43. Here, the infrared light irradiation unit 12 and the temperature variation measuring unit 13 illustrated in FIG. 3 in the inspection apparatus body 1 are disposed and supported so as to be located in the space between the first support member 41a and the second support member 41b and the space between the first support member 41a and the third support member 41c as illustrated in FIG. 13. This is intended so as not to cause the movable support member 41 to interfere with the optical path of the laser beam emitted from the infrared light irradiation unit 12 and the temperature variation measuring unit 13 and reflected from the internal wall surface of the tunnel 3.

Both ends of the arch shape of the movable support member 41 are provided with pedestal members 42 and 42. The pedestal member 42 enables the movable support member 41 to run on the road surface of the road 4 by itself, and includes a pedestal box 46 extending horizontally from the second support member 41b to the third support member 41c as illustrated in FIG. 13. Plural driving wheels 8 are linearly disposed in the pedestal box 46. The driving wheels 8 are made to rotate by an electric motor (not illustrated) disposed in the pedestal box 46. Since the pedestal member 42 including the driving wheels 8 is provided at each of both ends of the arch-like movable support member 41, the movable support member 41 is disposed to stand on the installation surface in a state in which the lower ends thereof are supported by both pedestal members 42. With the rotation of the driving wheels 8, the entire movable support member 41 can run in one direction or both forward and backward directions on the road surface by itself. That is, the self-running mechanism unit 40 of this embodiment includes the movable support member 41, the pedestal members 42, the electric motor, and the driving wheels 8.

In FIGS. 12 and 13, reference numeral 44 denotes a camera unit. The camera units 44 are movable along the arch shape of the second support member 41b and the third support member 41c using the second support member 41b and the third support member 41c as illustrated in FIG. 13 and the lens surface of the camera faces the internal wall surface of the tunnel 3 illustrated in FIG. 12. Accordingly, when an abnormal place is present on the internal wall surface of the tunnel 3, the abnormal place can be imaged by the camera unit 44.

In this state, by inserting the self-running mechanism unit 40 into the tunnel 3 so that the arch-like movable support member 41 is located along the internal wall surface of the tunnel 3 and the pedestal members 42 and 42 at both ends thereof are located on both sides of the road 4 in the tunnel 3 as illustrated in FIG. 12, the movable support member 41 is able to move forward and backward along the tunnel 3. The supply of power to the electric motor can be carried out using a known power supply unit such as a storage battery.

Figure 14:
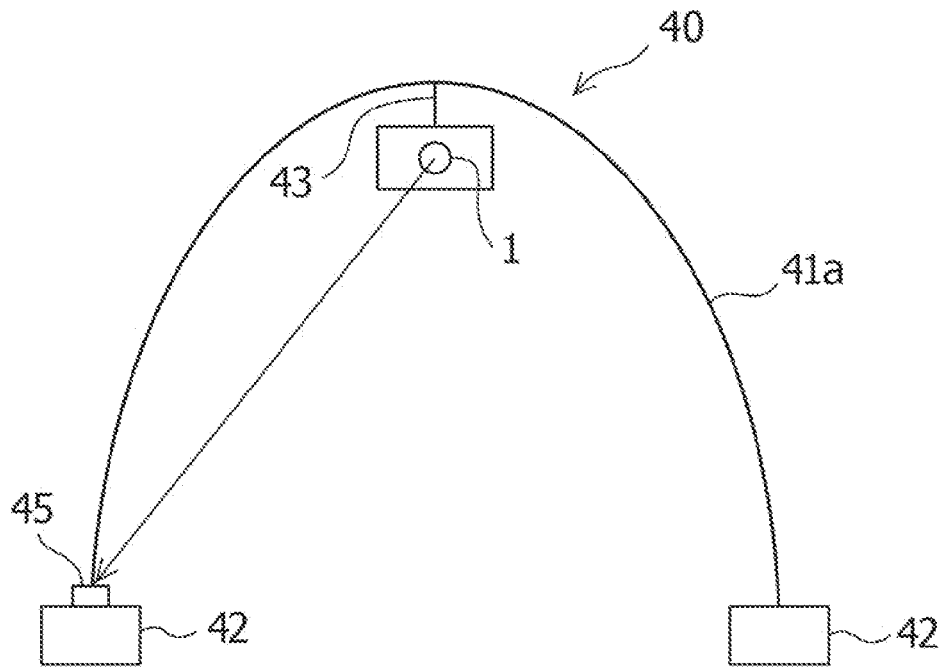
FIG. 14 is an explanatory diagram schematically illustrating an example in which the rotation of the infrared light irradiation unit and the temperature variation measuring unit of the inspection apparatus body in the self-running mechanism unit according to the second embodiment is detected.
Figure 15:
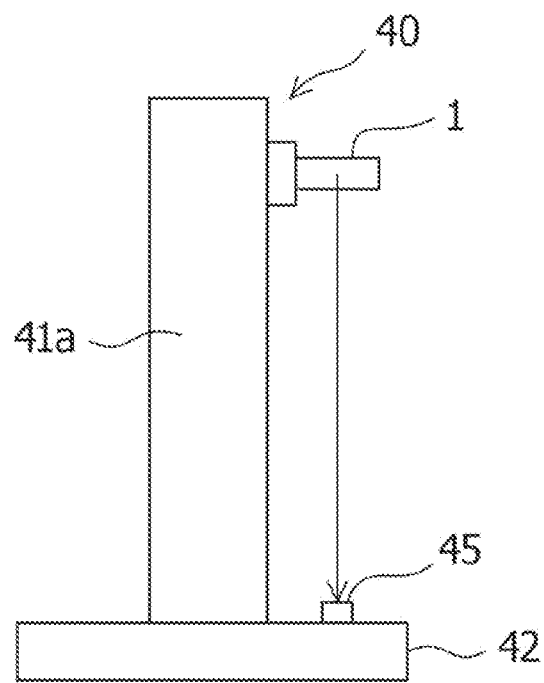
FIG. 15 is a side view of FIG. 14.

The operation of the inspection apparatus body 1 in this embodiment is the same as described above. However, in the self-running mechanism unit 40 of the second embodiment, the rotations of the infrared light irradiation unit 12 and the temperature variation measuring unit 13 of the inspection apparatus body 1 (see FIGS. 3 to 5) are detected as illustrated in FIGS. 14 and 15. That is, a high-reflectance member 45 is disposed on the top surface of the pedestal member 42 connected to the lower end of the first support member 41a supporting the inspection apparatus body 1, the reflected beams of the laser beams applied from the infrared laser chip 17 of the infrared light irradiation unit 12 and the laser beam receiving-and-emitting chip 20 of the temperature variation measuring unit 13 are received, and it is detected whether the infrared laser chip 17 and the laser beam receiving-and-emitting chip 20 are rotated and the rotation angles are measured. In this case, since the arch shape of the first support member 41a is an arch shape along the internal wall surface of the tunnel 3, the pseudo rotation angles of the infrared light irradiation unit 12 and the temperature variation measuring unit 13 with respect to the internal wall surface of the tunnel 3 can be measured by setting the position to which the high-reflectance member 45 is attached as zero-point positions of the rotation angles of the infrared laser chip 17 and the laser beam receiving-and-emitting chip 20. It is assumed that the temperature of the high-reflectance members 45 does not rise due to the absorption of heating infrared light from the infrared light irradiation unit 12.

Regarding the moved position of the inspection apparatus body 1 of the second embodiment in the longitudinal direction of the tunnel 3, for example, the high-reflectance member 23 illustrated in FIG. 7 is disposed in a continuous line shape or the high-reflectance members 23 are disposed with constant spacing along the longitudinal direction of the tunnel 3 and the reflected beam of the laser beam, which has been applied from the infrared light irradiation unit 12 or the temperature variation measuring unit 13, from the high-reflectance member 23 is detected, so that the position of the inspection apparatus body 1 in the longitudinal direction of the tunnel 3 can be detected. Accordingly, it is possible to detect the position of the inspection apparatus body 1 moving along the tunnel 3 to be inspected. In this case, it is also assumed that the high-reflectance member 23 does not rise due to the absorption of the heating infrared light from the infrared light irradiation unit 12.

The usage and operation of the nondestructive inspection apparatus including the self-running mechanism unit 40 of the second embodiment are basically the same as the usage and operation of the nondestructive inspection apparatus including the self-running mechanism unit 2 of the first embodiment, and both are different from each other only in the moving operation of the self-running mechanism unit 40 of the second embodiment. When the self-running mechanism unit 40 of the second embodiment illustrated in FIG. 12 is employed, it is not necessary to install the guide rail 6 for supporting the self-running mechanism unit 2 (see FIG. 1) of the first embodiment in the road 4 in the tunnel 3 to be inspected and it is thus easy to introduce the nondestructive inspection apparatus according to the invention. As long as the arch shape of the self-running mechanism unit 40 of the second embodiment matches the shape of the internal wall surface of the tunnel 3 to be inspected, it is possible to introduce the nondestructive inspection apparatus into the existing tunnel 3.

The self-running mechanism unit enabling the inspection apparatus body 1 to be movable along a structure to be inspected is not limited to the self-running mechanism unit 2 of the first embodiment or the self-running mechanism unit 40 of the second embodiment, but may have a configuration like a monorail in which a rail is installed in the longitudinal direction on the internal wall surface of the tunnel 3.

Figure 16:
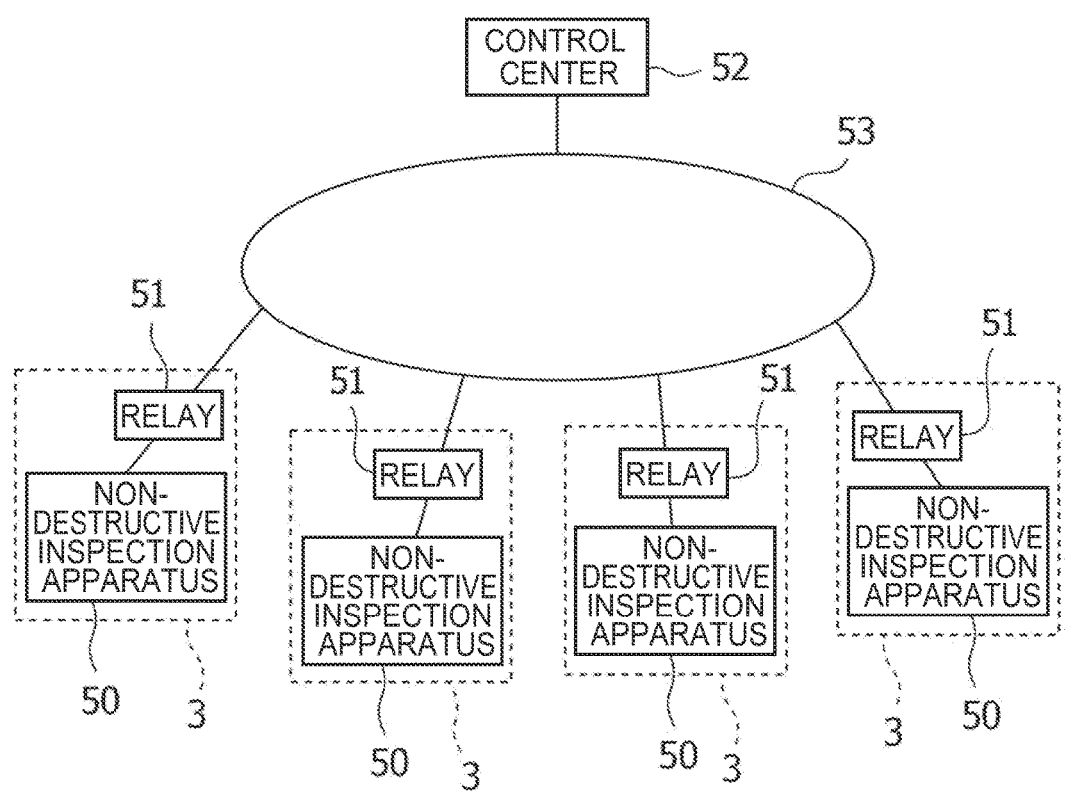
FIG. 16 is a block diagram illustrating an embodiment of an inspection system of a structure according to the present invention.

FIG. 16 is a block diagram illustrating an embodiment of an inspection system of a structure according to the present invention. The inspection system serves to inspect the structure for an internal defect by irradiating the structure to be inspected (a structure such as a tunnel or an elevated bridge) with infrared light and includes a nondestructive inspection apparatus 50, a relay 51, a control center 52, a bidirectional communication network 53. Reference numeral 3 denotes a tunnel as the structure to be inspected in which the nondestructive inspection apparatus 50 is arranged.

The nondestructive inspection apparatus 50 is the nondestructive inspection apparatus described above according to the present invention, has the configuration illustrated in FIGS. 1 and 12, and is arranged, for example, in the tunnel 3. As illustrated in FIG. 9, the nondestructive inspection apparatus 50 includes the infrared light irradiation unit 12 that irradiates the structure to be inspected with heating infrared light, the temperature variation measuring unit 13 that measures a variation in temperature of the structure due to the irradiation with infrared light from the infrared light irradiation unit 12, the drive-control-and-accumulation unit 14 that performs the drive control of the infrared light irradiation unit 12 and the temperature variation measuring unit 13 and the data accumulation, the self-running mechanism unit 2 that enables the casing, on which the infrared light irradiation unit 12, the temperature variation measuring unit 13, and the drive-control-and-accumulation unit 14 are mounted, to move along the structure, and the communication unit 27 that sends the inspection data acquired by the drive-control-and-accumulation unit 14 to the outside. The nondestructive inspection apparatus inspects the structure for an internal defect by irradiating the structure with heating infrared light and measuring the variation in temperature of the structure due to the irradiation with the infrared light while moving along the structure (3) to be inspected through the use of the self-running mechanism unit 2.

The relay 51 is disposed at an end portion of the tunnel 3 to be inspected (for example, a tunnel entrance or a tunnel exit), receives the inspection data transmitted from the nondestructive inspection apparatus 50, and includes a data communication unit that sends the received data to the bidirectional communication network 53. The disposed position of the relay 51 is not limited to the end portion of the tunnel 3 but may be installed at the center of the tunnel 3 or at a position outside the tunnel 3 immediately subsequent to the exit thereof.

The control center 52 receives and processes the inspection data sent from the nondestructive inspection apparatus 50 and includes a data processing unit such as a central processing unit (CPU). As illustrated in FIG. 16, when controlling plural nondestructive inspection apparatuses 50, the control center includes a host computer.

The bidirectional communication network 53 is disposed between the relay 51 and the control center 52, transmits and receives the inspection data, and includes a known bidirectional network so as to interchange the inspection data.

The nondestructive inspection apparatus 50, the relay 51, the bidirectional communication network 53, and the control center 52 may communicate with each other in a wired manner or a wireless manner. A data processing unit that processes the inspection data may be disposed in the relay 51 and the inspection data sent from the nondestructive inspection apparatus 50 may be processed and transmitted to the control center 52 by the relay 51.

In the inspection system, the nondestructive inspection apparatus 50 may be disposed in a single structure (tunnel 3) to be inspected and the nondestructive inspection apparatus 50 may be connected to the control center 52 via the relay 51 and the bidirectional communication network 53, but the nondestructive inspection apparatus 50 may be installed for each of the plural structures (tunnels 3) to be inspected as illustrated in FIG. 16, and a single control center 52 may be installed for the plural nondestructive inspection apparatuses 50 via the bidirectional communication network 53 so as to enable bidirectional communications.

Next, the usage and operation of the inspection system according to the present invention having the above-mentioned configuration will be described below. The usage and operation of the nondestructive inspection apparatus 50 are the same as described above according to the present invention. The inspection data collected for the internal wall surface of the respective tunnels 3 to be inspected by the nondestructive inspection apparatus 50 is sent to the relay 51 disposed at the entrance or the exit of the respective tunnels 3 and is sent to the control center 52 via the bidirectional communication network 53. The control center 52 receives the inspection data sent from the nondestructive inspection apparatus 50 disposed in each tunnel 3, processes the inspection data, and accumulates the processed inspection data. The inspection of the internal wall surface of each tunnel 3 is periodically performed every day or every predetermined period and it can be seen that a particular state occurs on the surface of the tunnel 3 or in the tunnel 3 when an inspection result different from the previous inspection data is acquired with the lapse of time, so that it is possible to inspect the structure for an internal defect. As described above, the relay 51 may be provided with the data processing unit that processes the inspection data and the relay 51 may process the inspection data sent from the nondestructive inspection apparatus 50 and may transmit the processed inspection data to the control center 52. In this case, the processing of the inspection data can be performed by only providing a small-scale data processing unit to the relay 51 for each tunnel 3 without providing a large-scale data processing unit to the control center 52.

It is possible to uniformly and automatically inspect the internal wall surfaces of the plural tunnels 3 by this operation of the inspection system. In this case, it is possible to nondestructively inspect the tunnels 3 at any time of a day without hindering the movement of other vehicles. Since the labor of an operator or the like is not necessary, it is possible to reduce inspection costs.

It should be noted that the entire contents of Japanese Patent Application No. 2013-182357, filed on Sep. 3, 2013, on which convention priority is claimed, is incorporated herein by reference.

It should also be understood that many modifications and variations of the described embodiments of the invention will be apparent to a person having an ordinary skill in the art without departing from the spirit and scope of the present invention as claimed in the appended claims.

What is claimed is:

1. A nondestructive inspection apparatus of a structure, comprising:
    an infrared light irradiation unit configured to irradiate a structure to be inspected with heating infrared light, and is independently rotatable about a horizontal rotation shaft;
    a temperature variation measuring unit configured to measure a variation in temperature of the structure due to the irradiation with infrared light from the infrared light irradiation unit, and is independently rotatable about the horizontal rotation shaft;
    a drive-control-and-accumulation unit configured to perform drive control of the infrared light irradiation unit and the temperature variation measuring unit and configured to perform data accumulation; and
    a self-running mechanism unit that enables a casing, on which the infrared light irradiation unit, the temperature variation measuring unit, and the drive-control-and-accumulation unit are mounted, to move along the structure,
    wherein the structure is configured to be inspected for an internal defect by irradiating the structure with heating infrared light while the nondestructive inspection apparatus moves along the structure to be inspected through the use of the self-running mechanism unit and measuring the variation in temperature of the structure due to the irradiation with infrared light.

2. The nondestructive inspection apparatus of a structure according to claim 1, wherein the infrared light irradiation unit is an infrared laser that oscillates configured to oscillate a heating laser beam.

3. The nondestructive inspection apparatus of a structure according to claim 1, wherein the temperature variation measuring unit is a laser beam receiving-and-emitting unit configured to irradiate the structure with a measuring laser beam and configured to detect the reflected beam thereof to determine the reflectance of the structure.

4. The nondestructive inspection apparatus of a structure according to claim 1, wherein the temperature variation measuring unit is an infrared light detector configured to determine an amount of infrared light emitted from the structure to measure the variation in temperature of the structure.

5. The nondestructive inspection apparatus of a structure according to claim 1, wherein the self-running mechanism unit is configured to support a support member of the casing using a guide rail installed on a road surface extending along the structure and to enable the support member to move on the road surface by guidance of the guide rail.

6. A nondestructive inspection apparatus of a structure, comprising:
    an infrared light irradiation unit configured to irradiate a structure to be inspected with heating infrared light;
    a temperature variation measuring unit configured to measure a variation in temperature of the structure due to the irradiation with infrared light from the infrared light irradiation unit;
    a drive-control-and-accumulation unit configured to perform drive control of the infrared light irradiation unit and the temperature variation measuring unit and configured to perform data accumulation; and a self-running mechanism unit that includes a casing, on which the infrared light irradiation unit, the temperature variation measuring unit, and the drive-control-and-accumulation unit are mounted, and a movable support member that is formed in an arch shape along an internal wall surface of the structure in which the internal wall surface has a cross-sectional shape of a semi-circular arc and that supports the casing, and is configured to enable pedestal members at both ends of the movable support member to move on a road surface by themselves, and that enables the casing to move the casing along the structure, wherein the structure is configured to be inspected for an internal defect by irradiating the structure with heating infrared light while the nondestructive inspection apparatus moves along the structure to be inspected through the use of the self-running mechanism unit and measuring the variation in temperature of the structure due to the irradiation with infrared light.

7. The nondestructive inspection apparatus of a structure according to claim 1, wherein the casing includes a monitoring camera configured to monitor a front side in a moving direction of the casing.

8. The nondestructive inspection apparatus of a structure according to claim 1, wherein the self-running mechanism unit is configured to move forward and backward along the structure and at least the infrared light irradiation unit and the temperature variation measuring unit are disposed as a pair for each direction of the movements.

9. An inspection system of a structure comprising:
a nondestructive inspection apparatus including an infrared light irradiation unit configured to irradiate a structure to be inspected with heating infrared light, and is independently rotatable about a horizontal rotation shaft, a temperature variation measuring unit configured to measure a variation in temperature of the structure due to the irradiation with infrared light from the infrared light irradiation unit, and is independently rotatable about the horizontal rotation shaft, a drive-control-and-accumulation unit configured to perform drive control of the infrared light irradiation unit and the temperature variation measuring unit and configured to perform data accumulation, a self-running mechanism unit that enables a casing, on which the infrared light irradiation unit, the temperature variation measuring unit, and the drive-control-and-accumulation unit are mounted, to move along the structure, and a communication unit configured to transmit inspection data acquired by the drive-control-and-accumulation unit to the outside, wherein the structure is configured to be inspected for an internal defect by irradiating the structure with heating infrared light while the nondestructive inspection apparatus moves along the structure to be inspected through the use of the self-running mechanism unit and measuring the variation in temperature of the structure due to the irradiation with infrared light;
a relay configured to receive the inspection data transmitted from the nondestructive inspection apparatus;
a control center configured to receive the inspection data transmitted from the nondestructive inspection apparatus and configured to process the inspection data; and
a bidirectional communication network that is disposed between the relay and the control center, and is configured to transmit and receive the inspection data.

10. The inspection system of a structure according to claim 9, wherein the inspection data transmitted from the nondestructive inspection apparatus is processed and transmitted to the control center through the use of the relay.

11. The inspection system of a structure according to claim 9, wherein the nondestructive inspection apparatus is installed for each of plural structures to be inspected, and the single control center is installed for the nondestructive inspection apparatus installed for each of the plural structures to be inspected via the bidirectional communication network.

12. An inspection system of a structure comprising:
a nondestructive inspection apparatus including an infrared light irradiation unit configured to irradiate a structure to be inspected with heating infrared light, a temperature variation measuring unit configured to measure a variation in temperature of the structure due to the irradiation with infrared light from the infrared light irradiation unit, a drive-control-and-accumulation unit configured to perform drive control of the infrared light irradiation unit and the temperature variation measuring unit and configured to perform data accumulation, a self-running mechanism unit that includes a casing, on which the infrared light irradiation unit, the temperature variation measuring unit, and the drive-control-and-accumulation unit are mounted, and a movable support member that is formed in an arch shape along an internal wall surface of the structure in which the internal wall surface has a cross-sectional shape of a semi-circular arc and that supports the casing, and is configured to enable pedestal members at both ends of the movable support member to move on a road surface by themselves, and that enables the casing to move along the structure, and a communication unit configured to transmit inspection data acquired by the drive-control-and-accumulation unit to the outside, wherein the structure is configured to be inspected for an internal defect by irradiating the structure with heating infrared light while the nondestructive inspection apparatus moves along the structure to be inspected through the use of the self-running mechanism unit and measuring the variation in temperature of the structure due to the irradiation with infrared light;
a relay configured to receive the inspection data transmitted from the nondestructive inspection apparatus
a control center configured to receive the inspection data transmitted from the nondestructive inspection apparatus and processes the inspection data; and
a bidirectional communication network that is disposed between the relay and the control center, and is configure to transmit and receive the inspection data.

13. The nondestructive inspection apparatus of a structure according to claim 6, wherein the infrared light irradiation unit is an infrared laser configured to oscillate a heating laser beam.

14. The nondestructive inspection apparatus of a structure according to claim 6, wherein the temperature variation measuring unit is a laser beam receiving-and-emitting unit configured to irradiate the structure with a measuring laser beam and configured to detect the reflected beam thereof to determine the reflectance of the structure.

15. The nondestructive inspection apparatus of a structure according to claim 6, wherein the temperature variation measuring unit is an infrared light detector configured to determine an amount of infrared light emitted from the structure to measure the variation in temperature of the structure.

16. The nondestructive inspection apparatus of a structure according to claim 6, wherein the self-running mechanism unit is configured to support a support member of the casing using a guide rail installed on a road surface extending along the structure and to enable the support member to move on the road surface by guidance of the guide rail.

17. The nondestructive inspection apparatus of a structure according to claim 6, wherein the casing includes a monitoring camera configured to monitor a front side in a moving direction of the casing.

18. The nondestructive inspection apparatus of a structure according to claim 6, wherein the self-running mechanism unit is configured to move forward and backward along the structure and at least the infrared light irradiation unit and the temperature variation measuring unit are disposed as a pair for each direction of the movements.

19. The inspection system of a structure according to claim 12, wherein the inspection data transmitted from the nondestructive inspection apparatus is processed and transmitted to the control center through the use of the relay.

20. The inspection system of a structure according to claim 12, wherein the nondestructive inspection apparatus is installed for each of plural structures to be inspected, and the single control center is installed for the nondestructive inspection apparatus installed for each of the plural structures to be inspected via the bidirectional communication network.

* * * * *

UNITED STATES PATENT AND TRADEMARK OFFICE
CERTIFICATE OF CORRECTION

PATENT NO. : 9,746,435 B2  
APPLICATION NO. : 14/475327  
DATED : August 29, 2017  
INVENTOR(S) : Koichi Kajiyama et al.

Page 1 of 1

It is certified that error appears in the above-identified patent and that said Letters Patent is hereby corrected as shown below:

In the Claims

In Column 16, Line 36:
Replace "that oscillates configured to oscillate" with --configured to oscillate--.

Signed and Sealed this
Twenty-fourth Day of September, 2019

Andrei Iancu
*Director of the United States Patent and Trademark Office*